United States Patent [19]

Child et al.

[11] Patent Number: 4,935,552

[45] Date of Patent: Jun. 19, 1990

[54] DUAL STAGE PROCESS FOR THE PRODUCTION OF ETHERS

[75] Inventors: Jonathan E. Child, Sewell; Byung C. Choi; Francis P. Ragonese, both of Cherry Hill, all of N.J.

[73] Assignee: Mobil Oil Corporation, New York, N.Y.

[21] Appl. No.: 296,112

[22] Filed: Jan. 12, 1989

[51] Int. Cl.$^5$ .................... C07C 41/09; C07C 41/05
[52] U.S. Cl. .................... 568/695; 568/696; 568/697; 568/698; 568/897
[58] Field of Search ............... 568/694, 695, 697, 698, 568/897

[56] References Cited

U.S. PATENT DOCUMENTS

| | | |
|---|---|---|
| 2,162,913 | 6/1939 | Eversole et al. |
| 2,477,380 | 7/1949 | Kreps et al. |
| 2,797,247 | 6/1957 | Keith |
| 2,798,097 | 7/1957 | Hettinger, Jr. et al. |
| 2,805,260 | 9/1957 | Keith |
| 2,830,090 | 4/1958 | Teter et al. |
| 2,861,045 | 11/1958 | Lauger et al. |
| 2,891,999 | 6/1959 | Langer, Jr. |
| 3,006,970 | 10/1961 | Beuther et al. |
| 3,198,752 | 8/1965 | Bridger et al. |
| 3,267,156 | 8/1966 | Hansen ........................ 568/698 |
| 3,686,334 | 8/1972 | Britton ........................ 568/896 |
| 3,810,849 | 5/1974 | Massle |
| 3,953,533 | 6/1976 | Sommer et al. ............... 568/896 |
| 3,989,762 | 11/1976 | Ester |
| 4,042,633 | 8/1977 | Woods |
| 4,175,210 | 11/1979 | Selwitz et al. |
| 4,182,914 | 1/1980 | Imaizumi |
| 4,214,107 | 7/1980 | Chang et al. |
| 4,334,890 | 6/1982 | Kochar et al. |
| 4,418,219 | 11/1983 | Hanes et al. |
| 4,423,251 | 12/1983 | Pujodo et al. ............... 568/697 |
| 4,439,409 | 3/1984 | Puppe et al. |
| 4,499,313 | 2/1985 | Okumura et al. |
| 4,551,567 | 11/1985 | Smith et al. ............... 568/698 |
| 4,579,984 | 4/1986 | Neier et al. ............... 568/897 |
| 4,605,787 | 8/1986 | Chu et al. |
| 4,714,787 | 12/1987 | Bell et al. |
| 4,731,489 | 3/1988 | Whisenhunt et al. |
| 4,783,555 | 11/1988 | Atkins |

FOREIGN PATENT DOCUMENTS 0055045  6/1982  European Pat. Off.

*Primary Examiner*—Howard T. Mars
*Attorney, Agent, or Firm*—Alexander J. McKillop; Charles J. Speciale; Malcolm D. Keen

[57] ABSTRACT

Light olefins are catalytically converted to ethers, e.g., propylene is converted to diisopropyl ether, in a dual stage process in which product ether is recycled to a first stage reaction zone to significantly reduce the operating temperature of the olefin hydration/etherification reactions taking place in that zone. Alcohol produced in the first stage reaction zone undergoes conversion in the second stage reaction zone, e.g., by etherification with light olefin or by catalytic distillation, to provide additional product ether. The process contemplates the use of zeolites as olefin hydration/etherification catalysts.

24 Claims, 2 Drawing Sheets

DUAL STAGE PROCESS FOR THE PRODUCTION OF ETHERS

CROSS REFERENCE TO RELATED APPLICATIONS

This application is related by subject matter to commonly assigned copending U.S. patent application Ser. Nos. 139,543; 139,557; 139,566; 139,567; and, 139,570, each filed Dec. 30, 1987. The contents of these applications, which are concerned with the production of alcohol(s) and/or ether(s), are incorporated by reference herein.

BACKGROUND OF THE INVENTION

This invention relates to a dual stage process for the catalytic conversion of olefin(s) to provide ether(s). More particularly, the invention relates to a process for the catalytic conversion of a feed containing one or more light olefins such as ethylene, propylene, butenes, pentenes, hexenes, heptenes, etc., in a first stage in the presence of recycled ether(s) to provide a mixture of alcohol(s) and ether(s), the alcohol(s) being subsequently converted in a second stage, e.g., by reaction with light olefin or by catalytic distillation, to provide ether(s). The ether(s) are useful, inter alia, as high octane blending stocks for gasoline.

There is a need for an efficient catalytic process to manufacture ethers from light olefins thereby augmenting the supply of high octane blending stocks for gasoline. Lower molecular weight ethers such as diisopropyl ether (DIPE) are in the gasoline boiling range and are known to have a high blending octane number In addition, by-product propylene from which DIPE can be made is usually available in a fuels refinery. The petrochemicals industry also produces mixtures of light olefin streams in the $C_2$ to $C_7$ molecular weight range and the conversion of such streams or fractions thereof to ethers can also provide products useful as solvents and as blending stocks for gasoline.

The catalytic hydration of olefins to provide alcohols and/or ethers is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; and, 3,989,762, among others.

Olefin hydration employing zeolite catalysts is known. As disclosed in U.S. Pat. No. 4,214,107, lower olefins, in particular, propylene, are catalytically hydrated over a porous crystalline aluminosilicate, or zeolite, catalyst having a silica to alumina ratio of at least 12 and a Constraint Index of from 1 to 12, e.g., ZSM-5 type zeolite, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y, each having a silica-alumina molar ratio of from 20 to 500. The use of such a catalyst is said to result in higher yields of alcohol than olefin hydration processes which employ conventional solid acid catalysts. Use of the catalyst is said to offer the advantage over ion-exchange type olefin hydration catalysts of not being restricted by the hydration temperature.

U.S. Pat. No. 4,783,555 describes an olefin hydration process employing a medium pore zeolite as hydration catalyst. Specific catalysts mentioned are Theta-1, said to be preferred, ferrierite, ZSM-22, ZSM-23 and NU-10.

Japanese Laid-Open patent application No. 60-246335 discloses the hydration of branched olefins to alcohols in the presence of a zeolite having a silica to alumina ratio of above 10.

The catalyzed reaction of olefins with alcohols to provide ethers is another well known type of process. As disclosed in U.S. Pat. No. 4,042,633, diisopropyl ether (DIPE) is prepared from isopropyl alcohol (IPA) employing montmorillonite clay catalysts, optionally in the presence of added propylene.

U.S. Pat. No. 4,182,914 discloses the production of DIPE from IPA and propylene in a series of operations employing a strongly acidic cation exchange resin as catalyst.

In U.S. Pat. No. 4,334,890, a mixed $C_4$ stream containing isobutylene is reacted with aqueous ethanol to form a mixture of ethyl tertiary butyl ether (ETBE) and tertiary butyl alcohol (TBA).

U.S. Pat. No. 4,418,219 discloses a process for preparing methyl tertiary butyl ether (MTBE) by reacting isobutylene and methanol in the presence of boron phosphate, blue tungsten oxide or a crystalline aluminosilicate zeolite having a silica to alumina mole ratio of at least 12:1 and a Constraint Index of from 1 to about 12 as catalyst.

As disclosed in U.S. Pat. No. 4,605,787, alkyl tertalkyl ethers such as MTBE and tertiary amyl methyl ether (TAME) are prepared by the reaction of a primary alcohol with an olefin having a double bond on a tertiary carbon atom employing as catalyst an acidic zeolite having a Constraint Index of from about 1 to 12, e.g., ZSM-5, ZSM-11, ZSM-12, ZSM-23 dealuminized zeolite Y and rare earth-exchanged zeolite Y.

U.S. Pat. No. 4,714,787 discloses the preparation of ethers by the catalytic reaction of linear monoolefins with primary or secondary alcohols employing, as catalyst, a zeolite having a pore size greater than 5 Angstroms, e.g., ZSM-5, zeolite Beta, zeolite X, zeolite Y, etc. Specifically, in connection with the reaction of propylene with methanol to provide methyl isopropyl ether (MIPE), effluent from the reactor is separated into a MIPE fraction, useful as a gasoline blending component, with unreacted propylene, methanol, by-product dimethyl ether (DME) and water at up to one mole per mole of by-product DME, either individually or in combination, being recycled to the reactor.

In European patent application No. 55,045, an olefin is reacted with an alcohol to provide an ether, e.g., isobutene and methanol are reacted to provide MTBE, in the presence of an acidic zeolite such as zeolite Beta, ZSM-5, ZSM-8, ZSM-11, ZSM-12, ZSM-23, ZSM-35, ZSM-43 and ZSM-48, and others, as catalysts.

German Patent No. 133,661 describes the reaction of isobutene and methanol to provide a mixture of products including MTBE, butanol and isobutene dimer employing acidic zeolite Y as catalyst.

Japanese Laid-Open patent application No. 59-2534 describes the reaction of a primary alcohol with a tertiary olefin in the presence of a zeolite having a silica to alumina mole ratio of at least 10 and the X-ray diffraction disclosed therein to provide a tertiary ether.

It is also known to produce mixtures of alcohols and ethers in a dual stage process.

Thus, in accordance with the process described in U.S. Pat. No. 4,731,489, isobutene and methanol are reacted in a first stage reaction zone in the presence of an acidic ion-exchange resin-type catalyst to provide MTBE which, together with water and additional isobutene, is converted by hydration and etherification reactions, primarily the former, in a second stage reaction zone, also in the presence of an acidic ion-exchange resin-type catalyst, to provide mainly tertiary butyl alcohol and MTBE.

SUMMARY OF THE INVENTION

It is an object of the present invention to provide a process for converting low cost, readily available sources of light olefins to ether(s) which can be used, inter alia, as high octane blending stocks for gasoline.

It is a particular object of the invention to convert a light olefin or mixture of such olefins by catalytic hydration to a mixture of alcohol(s) and ether(s) in a first stage reaction zone, separating the first stage product into an alcohol fraction and an ether fraction, converting the alcohol fraction to ether(s) in a second stage reaction zone and recycling at least a portion of the product ether(s) from the first and/or second stage reaction zone to the first stage reaction zone.

By way of realizing the foregoing and other objects of the invention, a process is provided for producing an ether which comprises:

(a) contacting a feed containing at least one light olefin with water, ether recycle and an olefin hydration/etherification catalyst under olefin hydration/etherification reaction conditions in a first stage reaction zone to provide a mixture of alcohol and ether;

(b) separating the effluent from the first stage reaction zone into an alcohol fraction and an ether fraction;

(c) converting at least a portion of the alcohol fraction in a second stage reaction zone to an ether; and, (d) recycling at least a portion of the ether fraction from step (b) and/or the ether product from step (c) to the first stage reaction zone.

Recycle of ether to the first stage reaction zone provides several advantages over an olefin hydration operation which omits this step. Thus, ether recycle serves to reduce the temperature of the olefin hydration operation taking place in the first stage reaction zone and tends to suppress the formation of ether in that zone, another factor contributing to maintaining a relatively low temperature in the first stage reaction zone. Ether recycle facilitates temperature management within the first stage reaction zone permitting one to emphasize conversion of olefin to ether and minimize oligomerization within this zone. Reduced temperature operation in the first stage reaction zone also permits the use of simple adiabatic reactors to accomplish olefin hydration.

DESCRIPTION OF THE PREFERRED EMBODIMENTS

Figure 1:
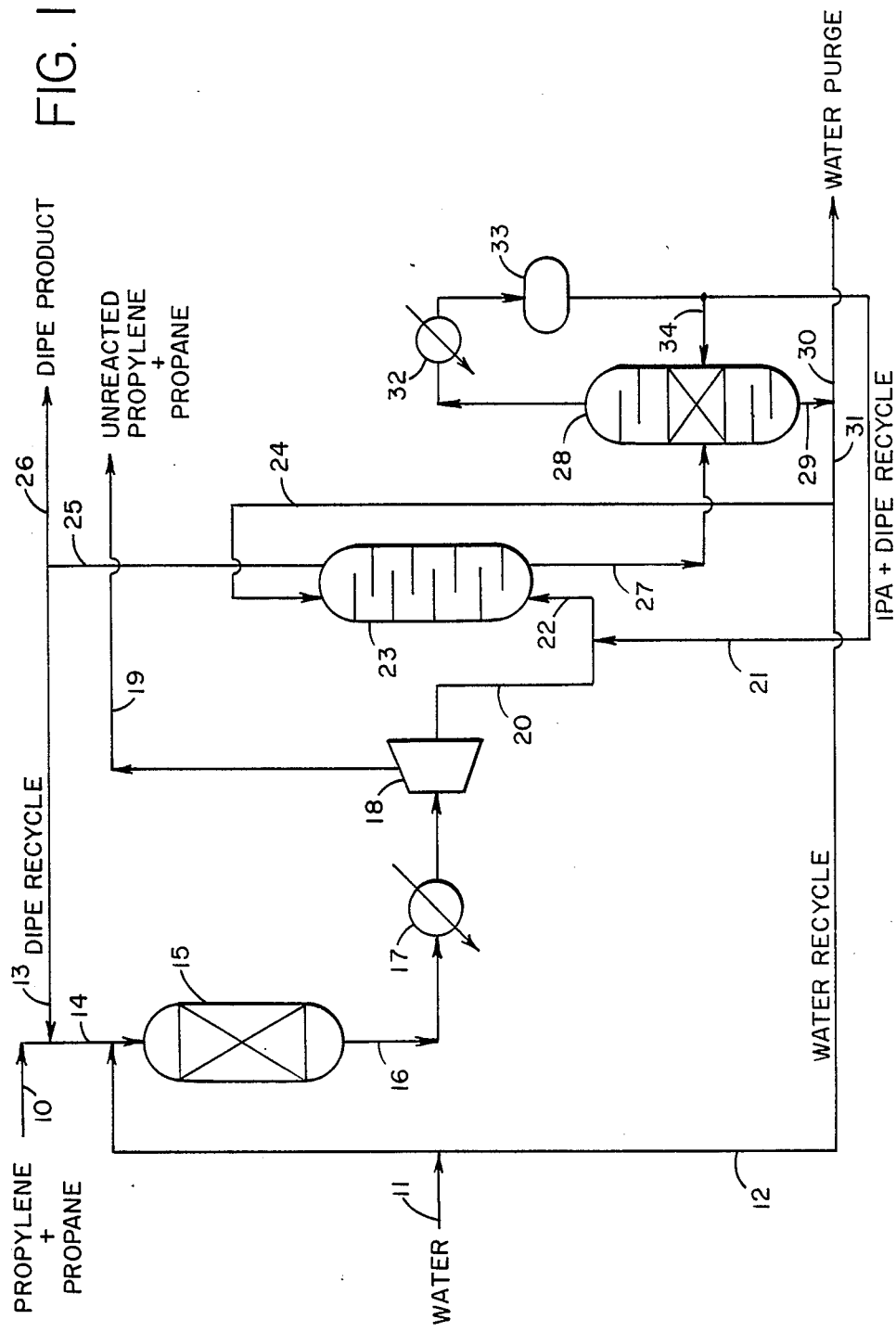
FIG. 1 illustrates a schematic flow arrangement of an embodiment of the dual stage process for producing ethers of this invention; and, FIG. 2 shows the temperature profiles within the first stage reaction zone of the process illustrated in FIG. 1 when operated with and without ether recycle to said zone.

The present invention is applicable to the conversion of individual light olefins and mixtures of light olefins of various structures, preferably within the $C_{2-7}$ range, to ethers. Accordingly, the invention is applicable to the conversion of ethylene, propylene, butenes, pentenes, hexenes and heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc.

For example, a typical FCC light olefin stream possesses the following composition:

| Typical Refinery FCC Light Olefin Composition | | |
|---|---|---|
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |
| Isobutene | 12.9 | 10.3 |
| n-Butane | 3.3 | 2.6 |
| Butenes | 22.1 | 18.3 |
| Pentanes | 0.7 | 0.4 |

A. The First Stage Reaction Zone

Catalytic conversion of light olefin in the first stage reaction zone involves reaction of olefin with water to provide alcohol (hydration) in accordance with the equation:

$$C_nH_{2n} + H_2O \rightleftharpoons C_nH_{2n+1}OH \qquad (1)$$

and reaction of olefin with alcohol to provide ether (etherification) in accordance with the equation

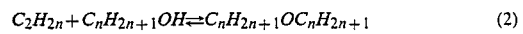

$$C_2H_{2n} + C_nH_{2n+1}OH \rightleftharpoons C_nH_{2n+1}OC_nH_{2n+1} \qquad (2)$$

A critical requirement in the operation of the first stage reaction zone is that the foregoing hydration and etherification reactions take place in the presence of recycled ether. The quantity of recycled ether will ordinarily be such as to result in a significant reduction in the operating temperature of the first stage reaction zone compared to an olefin hydration/etherification operation which is carried out under identical conditions but in the absence of recycled ether. Advantageously, the amount of recycled ether will be such as to reduce the steady-state operating temperature of the first stage by at least about 25° F., and preferably by at least about 80° F. Stated in terms of the total amount of olefin, water and recycled ether introduced to the first stage reaction zone, the ether can represent from about 2 to about 20 mole percent, and preferably from about 5 to about 10 mole percent, of such total. Stated yet another way, the mole ratio of recycled ether to feed olefin in the first stage reaction zone can vary from about 0.07 to about 0.4, and preferably from about 0.15 to about 0.3.

Ordinarily, with ether recycle, the temperature rise in the first stage reaction zone will be limited to within about 10° to about 80° F., and preferably to within about 20° to about 70° F. Aside from operating temperature and the amount of ether recycle required to maintain the operating temperature, the other conditions of the first stage reaction zone are not particularly critical. They include a total system pressure of from about 500 to about 3500 psig, preferably from about 800 to about 2500 psig and more preferably from about 1000 to about 1500 psig, a water to total olefin mole ratio of from about 0.1 to about 30, preferably from about 0.2 to about 15 and most preferably from about 0.3 to about 5. Depending on the nature of the olefin hydration/etherification catalyst employed and similar factors, it may be preferable to operate the first stage reaction zone at low water to olefin mole ratios as disclosed in U.S. patent application Ser. No. 139,567 referred to above, e.g., at water to olefin mole ratios of less than about 1.

The olefin hydration/etherification reactions taking place in the first stage reaction zone can be carried out under liquid phase, vapor phase or mixed vapor-liquid phase conditions in batch or continuous manner using a stirred tank reactor or fixed bed flow reactor, e.g., of the trickle-bed, liquid-up-flow, liquid-down-flow, counter-current, co-current, etc., type with a liquid hourly space velocity (LHSV) of from about 0.1 to about 10 being entirely suitable.

While any known or conventional olefin hydration-/etherification catalyst can be used in the first stage reaction zone, it is especially advantageous to employ a zeolite which is effective for the catalysis of olefin hydration/etherification to provide alcohols(s) and ether(s). Useful zeolite catalysts include those disclosed in the prior art discussed above as well as in pending U.S patent application Nos. 139,557, 139,567 and 139,570 referred to above.

For purposes of this invention, the term "zeolite" is meant to include the class of porotectosilicates, i.e., porous crystalline silicates, which contain silicon and oxygen atoms as the major components. Other components can be present in minor amounts, usually less than 14 mole %, and preferably less than 4 mole %. These components include aluminum, gallium, iron, boron, and the like, with aluminum being preferred. The minor components can be present separately or in mixtures in the catalyst. They can also be present intrinsically in the framework structure of the catalyst.

Representative of the zeolites which are preferred for use herein as olefin hydration/etherification catalysts are zeolite Beta, zeolite X, zeolite L, zeolite Y, ultrastable zeolite Y (USY), dealuminized Y (Deal Y), mordenite, ZSM-3, ZSM-4, ZSM-5, ZSM-12, ZSM-20, ZSM-23, ZSM-38, ZSM-50, MCM-22 and mixtures of any of the foregoing.

Also included within the definition of the useful zeolites are crystalline porous silicoaluminophosphates such as those disclosed in U.S. Pat. No. 4,440,871, the catalytic behavior of which is similar to that of the aluminosilicate zeolites.

Zeolite Beta is described in U.S. Reissue Pat. No. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192, 3,354,077, 3,375,065, 3,402,996, 3,449,070 and 3,595,611, to which reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U.S. Pat. No. 3,415,736, to which reference is made for details of this catalyst.

Zeolite ZSM-5 is described in U.S. Pat. Re. No. 29,948 (of original U.S. Pat. No. 3,702,886), to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-23 is described in U.S. Pat. No. 4,076,842, to which reference is made for the details of this catalyst.

Zeolite ZSM-35 is described in U.S. Pat. No. 4,016,245, to which reference is made for the details of this catalyst.

Zeolite ZSM-38 is described in U.S. Pat. No. 4,046,859, to which reference is made for the details of this catalyst.

Zeolite ZSM-50 is described in U.S. Pat. No. 4,640,829, to which reference is made for details of this catalyst.

Zeolite MCM-22 and the use of this zeolite to catalyze the reaction of olefin(s) with water to provide alcohol(s), ether(s) or mixtures thereof is disclosed in U.S. patent application Ser. No. 139,557 referred to above.

Zeolite MCM-22, or simply "MCM-22", appears to be related to the composition named "PSH-3" described in U.S. Pat. No. 4,439,409. Zeolite MCM-22 does not appear to contain all the components apparently present in the PSH-3 compositions. Zeolite MCM-22 is not contaminated with other crystal structures, such as ZSM-12 or ZSM-5, and exhibits unusual sorption capacities and unique catalytic utility when compared to the PSH-3 compositions synthesized in accordance with U.S. Pat. No. 4,439,409.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area (greater than 400 m$^2$/gm as measured by the BET [Bruenauer, Emmet and Teller] test) and unusually large sorption capacity when compared to previously described crystal structures having similar X-ray diffraction patterns. As is evident from the above formula, MCM-22 is synthesized nearly free of Na cations It can, therefore, be used as an olefin hydration/etherification catalyst with acid activity without an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for olefin hydration/etherification. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern which is distinguished from the patterns of other known crystalline materials by the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W | more specifically by the lines listed in Table II below:

TABLE II

| Interplanar d-Spacing (A) | Relative Intensity, I/Io × 100 |
|---|---|
| 30.0 ± 2.2 | W-M |
| 22.1 ± 1.3 | W |
| 3.91 ± 0.07 | M-VS | and yet more specifically by the lines listed in Table III below:

TABLE III

| Interplanar d-Spacing (A) | Relative Intensity, I/Io × 100 |
|---|---|
| 30.0 ± 2.2 | W-M |
| 22.1 ± 1.3 | W |
| 6.00 ± 0.1 | W-M |
| 4.06 ± 0.07 | W-S |
| 3.91 ± 0.07 | M-VS |

Most specifically, the calcined crystalline material has an X-ray diffraction pattern which includes the lines listed in Table IV below:

TABLE IV

| Interplanar d-Spacing (A) | Relative Intensity, I/Io × 100 |
|---|---|
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |

TABLE IV-continued

| Interplanar d-Spacing (A) | Relative Intensity, I/Io × 100 |
|---|---|
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/$I_o$, where $I_o$ is the intensity of the strongest line or peak, and d (obs.) the interplanar spacing in Angstroms Units (A), corresponding to the recorded lines, were determined. In Tables I–IV, the relative intensities are given in terms of the symbols W=weak, M=medium, S=strong and VS=very strong. In terms of intensities, these may be generally designated as follows

| | |
|---|---|
| W = | 0–20 |
| M = | 20–40 |
| S = | 40–60 |
| VS = | 60–100 |

It should be understood that these X-ray diffraction patterns are characteristic of all species of the present crystalline composition. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–80 | 10–60 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound H$_2$O of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of SiO$_2$, 8.9 wt. % Na$_2$O and 62.3 wt. % H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt. % solid YO$_2$, e.g., silica, and more preferably at least about 40 wt. % solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine which has the following structural formula:

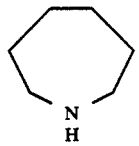

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

The zeolite olefin hydration/etherification catalysts selected for use herein will generally possess an alpha value of at least about 1. "Alpha value", or "alpha number", is a measure of zeolite acidic functionality and is more fully described together with details of its measurement in J. Catalysis, 61, pp. 390–396 (1980). Zeolites of relatively low acidity (e.g., zeolites possessing alpha values of less than about 200) can be prepared by a variety of techniques including (a) synthesizing a zeolite with a high silica/alumina ratio, (b) steaming, (c) steaming followed by dealuminization and (d) substituting framework aluminum with other trivalent metal species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with from about 10 to about 200 atmospheres. Specific details of several steaming procedures may be gained from the disclosures of U.S. Pat. Nos. 4,325,994, 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

Prior to their use as olefin hydration/etherification catalysts, the as-synthesized zeolite crystals should be subjected to thermal treatment to remove part or all of any organic constituent present therein. In addition, the zeolites should be at least partially dried prior to use. This can be done by heating the crystals to a temperature in the range of from about 200° C. to about 595° C. in an inert atmosphere, such as air, nitrogen, etc. and atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

The zeolite olefin hydration/etherification catalysts herein, especially in their metal, hydrogen and ammonium forms, can be beneficially converted to other forms by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

The original cations associated with the zeolites utilized herein can be replaced by a wide variety of other cations according to techniques well known in the art, e.g., by ion-exchange. Typical replacing cations include hydrogen, ammonium, alkyl ammonium and metal cations, and their mixtures. Metal cations can also be introduced into the zeolite. In the case of metal cations, particular preference is given to metals of Groups IB to VIII of the Periodic Table including, by way of example, iron, nickel, cobalt, copper, zinc, platinum, palladium, calcium, chromium, tungsten, molybdenum, rare earth metals, etc. These metals can also be present in the form of their oxides.

A typical ion-exchange technique involves contacting a particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251 and 3,140,253.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

It can be advantageous to incorporate the abovedescribed zeolite catalysts into some other material, i.e., a matrix or binder, which is resistant to the temperature and other conditions employed in the first stage reaction zone. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite olefin hydration/etherification catalyst can be composited with a porous metal oxide binder material such as alumina, titania, zirconia, silica, silica-alumina, silica-magnesia, silica-zirconia, silica-thoria, silica-beryllia, silica-titania, etc., as well as ternary oxides compositions such as silica-alumina-thoria, silica-alumina-zirconia, silica-alumina-magnesia, silica-magnesia-zirconia, etc. The binder material can be in the form of a cogel.

In some cases, it may be advantageous to employ as the binder material, one or more essentially non-acidic oxides of metals of Groups IVA and/or IVB of the Periodic Table of the Elements. Particularly useful are the oxides of silicon, germanium, titanium and zirconium with titanium and zirconium being preferred. Combinations of such oxides with other oxides including such relatively acidic oxides as alumina are also useful provided that at least about 40 weight percent, and preferably at least 50 weight percent, of the total metal oxide binder is one or a combination of the aforesaid Group IVA and/or Group IVB metal oxides. Thus, mixtures of oxides which can be used to provide the binder material herein include titania-alumina, titania-magnesia, titania-zirconia, titania-thoria, titania-beryllia, titania-silica-thoria, silica-alumina-zirconia, silica-alumina-magnesia, silica-titania-zirconia, and the like. It may be further advantageous to provide at least part of the Group IVA and/or IVB metal oxide binder, e.g., an amount representing from 1 to 100 weight percent and preferably from about 2 to about 60 weight percent of the total binder material, in colloidal form so as to facilitate the extrusion of the zeolite bound therewith.

The relative proportions of zeolite and metal oxide binder or other materix material on an anhydrous basis can vary widely with the zeolite content ranging from between about 1 to about 99 weight percent, and more usually in the range of from about 5 to about 90 weight percent, of the dry composite.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

Following the zeolite-catalyzed conversion of olefin to a mixture of alcohol(s) and ether(s) in the first stage reaction zone, the effluent from said zone is separated into a product alcohol(s) fraction and a product ether(s) fraction employing any suitable separation technique. Procedures which are especially advantageous for achieving such separation are described in U.S. patent application Ser. Nos. 139,543 and 139,566 referred to above. For example, in the case of the process disclosed in Ser. No. 139,543, effluent from a propylene hydration reactor containing propane (a non-reactive material originally present in the propylene feed), unreacted propylene, isopropyl alcohol (IPA), diisopropyl ether (DIPE) and water are passed to a separator unit with propane and unconverted propylene being recycled to the hydration reactor, part of the gaseous mixture being purged in order to avoid accumulation of propane in the recycle loop. The liquid products from the separator unit are introduced into a distillation unit where an azeotropic mixture of IPA, DIPE, water and propylene oligomers (mostly $C_6$ olefin) is distilled off and, following cooling, is introduced into a decanter in which phase separation takes place. The upper layer contains mostly DIPE, e.g., 90 weight percent or more, and relatively little water, e.g., 1 weight percent or so. The lower layer is largely water containing negligible quantities of IPA and DIPE. The bottom fraction of the distillation unit, mainly IPA, is, in accordance with the present invention, converted in a second stage reaction zone to DIPE. Recycle DIPE for introduction into the first stage reaction zone can be taken from the upper DIPE-containing layer formed in the decanter and/or from the DIPE product formed in the second stage reaction zone.

In accordance with the alcohol-ether separation procedure disclosed in Ser. No 139,566, again as applied to an IPA-DIPE propylene hydration/etherification product effluent, the effluent is passed to a separator operating below the propylene hydration/etherification conversion temperature. There, two liquid phases form, the aqueous phase being removed and, if desired, being recycled to the hydration/etherification reactor. The hydrocarbon-rich phase is flashed to a lower pressure to effect separation of any unreacted $C_3$ components. The flashed product, now containing a substantial amount of IPA product, is introduced to a distillation unit operated at or below atmospheric pressure to effect further purification of the DIPE. The azeotropic IPA, DIPE and water overhead product containing a small amount of propylene oligomer is condensed and thereafter contacted with reactor feed water. The resulting phase separation provides a DIPE product containing at most negligible amounts of IPA and water, e.g., 10 weight percent and 0.5 weight percent of these materials, respectively.

B. The Second Stage Reaction Zone

Product alcohol recovered from the first stage reaction zone can be converted to an ether by a variety of chemical procedures including reaction with olefin in the presence of an etherification catalyst in accordance with equation 1, supra, and catalytic distillation over a strong acid catalyst which involves a dehydration mechanism in accordance with the equation $$2C_nH_{2n+1}OH \rightleftharpoons C_nH_{2n+1}OC_nH_{2n+1} + H_2O \tag{3}$$

In the case of etherification, alcohol produced in the first stage reaction zone and separated from co-produced ether, e.g., employing any of the separation procedures described above, is reacted with a suitable catalyst such as one of the zeolites previously mentioned or some other etherification catalyst, e.g., a strongly acidic cation-exchange resin. When a zeolite catalyst is employed, the reaction conditions can be within the limits disclosed above for the operation of the first stage reaction zone. In the case of a strongly acidic cation-exchange resin and particularly where the alcohol undergoing conversion is isopropyl alcohol, the process described in U.S. Pat. No. 4,182,914, the contents of which are incorporated by reference herein, can be advantageously employed.

In the case of catalytic distillation, the operational parameters of this type of conversion process are well known and include the use of a strong acid at elevated temperatures, e.g., from about 250° to about 500° F. and preferably from about 300° to about 400° F. and moderate pressures, e.g., from 0 to about 500 psig and preferably from about 10 to about 100 psig.

The following example is illustrative of the present dual stage process for the production of ethers. The example specifically illustrates the conversion of a refinery stream containing approximately 70 weight percent propylene and 30 weight percent n-propane to diisopropyl ether (DIPE). All parts stated are by mole.

EXAMPLE

As shown in FIG. 1, a feed containing 362.0 moles propylene and 155.0 moles n-propane in line 10, 181.0 moles of feed water in line 11, 543 moles of recycle water in line 12 (for a total water to propylene mole ratio of 2:1) and 92.3 moles of recycled DIPE (for a mole ratio of DIPE to propylene of 0.25:1) in line 13 are introduced through line 14 into first stage olefin hydration reactor 15 operated under the following conditions:

| Olefin Hydration Catalyst | 35 weight percent alumina/ 65 weight percent zeolite |
|---|---|
| Temperature (inlet) | 300° F. |
| Pressure | 1500 psig |
| LHSV (based on propylene) | .5 |

Figure 2:
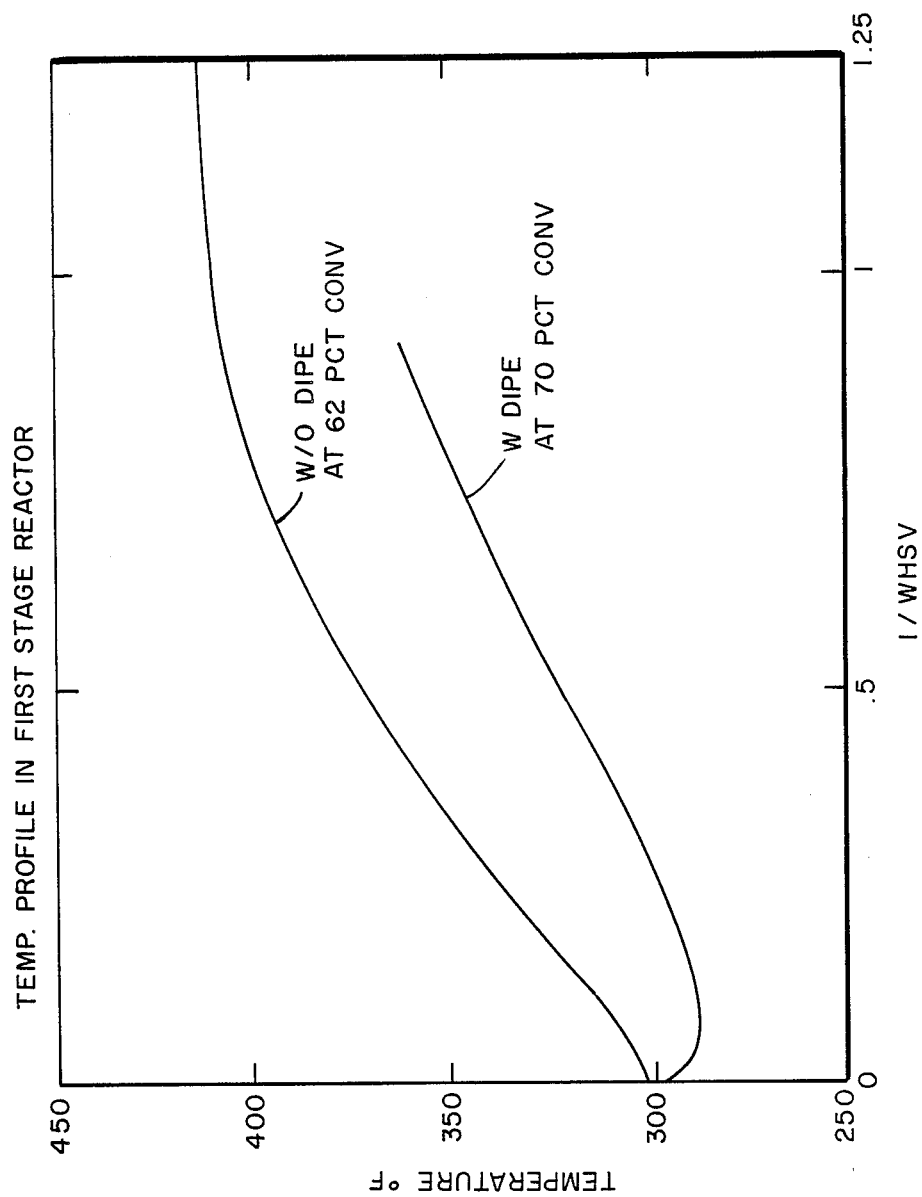

The influence of recycled DIPE on the temperature profile of first stage olefin hydration reactor 15 is graphically shown in FIG. 2. Thus, compared with operation of reactor 15 without recycled DIPE, the use of recycled DIPE in accordance with this invention and under the conditions stated results in a reduction in the temperature rise within reactor 15 of about 50° F.

Reactor effluent in line 16 possesses the following composition:

| Component | Moles |
|---|---|
| Unreacted Propylene | 123.1 |
| Propane | 155.0 |
| Unreacted Water | 458.9 |
| IPA | 291.3 |
| DIPE | 66.0 |

Following passage through exchanger 17 and expander 18, the unreacted propylene and propane are recovered through line 19 where they may be subjected to further processing for recovery of an essentially pure propylene component part or all of which can be recycled to process. The aqueous mixture of IPA and DIPE in line 20 and recycled IPA and DIPE in line 21 are introduced through line 22 into the bottom of extraction column 23 and recycled water (269.1 moles) in line 24 is introduced into the top of the column. Overheads from column 23, essentially pure DIPE, in line 25 is split into a recovered product stream in line 26 (120.0 moles) and a recycled stream (92.3 moles) in line 13 for introduction into first stage olefin hydration reactor 15. Bottoms from column 23, an aqueous mixture of IPA and DIPE, is introduced through line 27 into second stage catalytic distillation column 28. Catalytic distillation column 28 is operated under the following conditions:

| Alcohol Dehydration Catalyst | Amberlyst-15 |
|---|---|
| Temperature | 300° F. |
| Pressure | 50 psig |

The aqueous bottoms from column 28 in line 29 is divided into an aqueous purge stream 30 (61.0 moles) and an aqueous recycle stream which itself is divided into the aforementioned aqueous recycle stream fed through line 24 as overheads into extraction column 23 and the aforementioned aqueous recycle stream fed through lines 12 and 14 into first stage olefin hydration reactor 15. A portion of the mixture of IPA (949.8 moles) and DIPE (435.6 moles) obtained in column 28 following cooling in exchanger 32 and total condensor 33 is split into a reflux stream which is reintroduced into column 28 through line 34, and the aforementioned IPA/DIPE recycle stream is introduced through lines 21 and 22 into the bottom of extraction column 23.

What is claimed is:

1. A process for producing an ether which comprises:
    (a) contacting a feed containing at least one light olefin with water, ether recycle and an olefin hydration/etherification catalyst under olefin hydration/etherification conditions in a first stage reaction zone to provide an effluent comprising a mixture of alcohol and ether;
    (b) removing untreated olefin from the effluent and then extracting the effluent with water in an extraction zone to form (i) an aqueous extract comprising water and alcohol and (iii) either product;
    (c) converting at least a portion of the alcohol in the aqueous extract in a second stage reaction zone to an ether by dehydration in the presence of a dehydration catalyst to form a water and a dehydration effluent comprising ether product and alcohol;
    (d) separating the water formed in the second stage reaction zone from the dehydration effluent;
    (e) passing the dehydration effluent to the extraction zone;
    (f) extracting the dehydration effluent in the extraction zone with water to recover ether product produced by dehydration in the dehydration zone and produce aqueous extract of alcohol and water;
    (e) recycling at least a portion of the ether product to the first stage reaction zone.

2. The process of claim 1 wherein the olefin component of the feed contains from two to seven carbon atoms.

3. The process of claim 1 wherein the olefin feed contains at least one olefin selected from the group consisting of ethylene, propylene, butenes, pentenes, hexenes and heptenes.

4. The process of claim 1 wherein the olefin feed contains propylene and the product ether is diisopropyl ether.

5. The process of claim 1 wherein the olefin feed contains an isoolefin.

6. The process of claim 1 wherein the olefin feed contains isobutylene and the product ether is diisobutyl ether.

7. The process of claim 1 wherein the mole ratio of water to total olefin in the first stage reaction zone is from about 0.1 to about 30.

8. The process of claim 1 wherein the mole ratio of water to total olefin in the first stage reaction zone is from about 0.2 to about 15.

9. The process of claim 1 wherein the mole ratio of water to total olefin in the first stage reaction zone is from about 0.3 to about 5.

10. The process of claim 1 wherein the amount of recycled ether added to the first stage reaction zone is sufficient to reduce the operating temperature of said reaction zone by at least about 25° F.

11. The process of claim 1 wherein the amount of recycled ether added to the first stage reaction zone is sufficient to reduce the operating temperature of said reaction zone by at least about 80° F.

12. The process of claim 1 wherein ether recycle represents from about 2 to about 20 mole percent of the combined olefin, water and ether recycle introduced into the first stage reaction zone.

13. The process of claim 1 wherein ether recycle represents from about 5 to about 10 mole percent of the combined olefin, water and ether recycle introduced into the first stage reaction zone.

14. The process of claim 1 wherein the mole ratio of recycled ether to feed olefin in the first stage reaction zone is from about 0.07 to about 0.4.

15. The process of claim 1 wherein the mole ratio of recycled ether to feed olefin in the first stage reaction zone is from about 0.15 to about 0.3.

16. The process of claim 1 wherein the total system pressure of the first stage reaction zone is from about 500 to about 3500 psig.

17. The process of claim I wherein the total system pressure of the first stage reaction zone is from about 800 to about 2500 psig.

18. The process of claim 1 wherein the total system pressure of the first stage reaction zone is from about 1000 to about 1500 psig.

19. The process of claim 1 wherein the olefin hydration/etherification catalyst is an acidic zeolite catalyst.

20. The process of claim 19 wherein the zeolite is selected from the group consisting of mordenite, zeolite Beta, zeolite Y, USY, X, ZSM-3, ZSM-4, ZSM-5 ZSM-12, ZSM-20, ZSM-23, ZSM-38, ZSM-50 and MCM-22.

21. The process of claim 1 wherein the zeolite is composited with a binder.

22. The process of claim 1 wherein the zeolite is composited with a metal oxide binder.

23. The process of claim 1 wherein a non-zeolite catalyst which is effective for the hydration/etherification of light olefin is also present in the first stage reaction zone.

24. The process of claim 1 wherein in step (c), alcohol is converted to ether by catalytic distillation.

* * * * *